(12) United States Patent
Zablocki et al.

(10) Patent No.: US 7,732,595 B2
(45) Date of Patent: *Jun. 8, 2010

(54) PROCESS FOR PREPARING AN $A_{2A}$-ADENOSINE RECEPTOR AGONIST AND ITS POLYMORPHS

(75) Inventors: Jeff Zablocki, Mountain View, CA (US); Elfatih Elzein, Fremont, CA (US)

(73) Assignee: Gilead Palo Alto, Inc., Foster City, CA (US)

( * ) Notice: Subject to any disclaimer, the term of this patent is extended or adjusted under 35 U.S.C. 154(b) by 168 days.

This patent is subject to a terminal disclaimer.

(21) Appl. No.: 11/701,699

(22) Filed: Feb. 2, 2007

(65) Prior Publication Data

US 2007/0265445 A1 Nov. 15, 2007

Related U.S. Application Data

(60) Provisional application No. 60/801,857, filed on May 18, 2006, provisional application No. 60/765,114, filed on Feb. 3, 2006.

(51) Int. Cl.
*C07H 19/167* (2006.01)
(52) U.S. Cl. ............... 536/27.11; 536/27.63; 536/27.7
(58) Field of Classification Search ............... None
See application file for complete search history.

(56) References Cited

U.S. PATENT DOCUMENTS 6,403,567 B1    6/2002  Zablocki et al.
6,642,210 B1 *  11/2003 Zablocki et al. ............... 514/46
7,183,264 B2 *  2/2007  Zablocki et al. ............... 514/46

OTHER PUBLICATIONS

Niiya K. et al, "2-(N'-Alkylidenehydrazino) Adenosines: Potent and Selective Coronaryvasodilators", *Journal of Medicinal Chemistry*, American Chemical Society. Washington, vol. 35, No. 24, 1992, pp. 4557-4561.

* cited by examiner

*Primary Examiner*—Lawrence E Crane
(74) *Attorney, Agent, or Firm*—Swiss Tanner, P.C.

(57) ABSTRACT

Disclosed is a synthesis suitable for large scale manufacture of an $A_{2A}$-adenosine receptor agonist, and also relates to polymorphs of that compound, and to methods of isolating a specific polymorph. The $A_{2A}$-adenosine receptor agonist has the following formula:

This compound is prepared by reacting the ethyl ester with methylamine in a sealed pressure reactor.

13 Claims, 5 Drawing Sheets

PROCESS FOR PREPARING AN $A_{2A}$-ADENOSINE RECEPTOR AGONIST AND ITS POLYMORPHS

This application claims priority to U.S. Provisional Patent Application Ser. No. 60/801,857, filed May 18, 2006 and now abandoned, and to U.S. Provisional Patent Application Ser. No. 60/765,114, filed Feb. 3, 2006 and now abandoned, the complete disclosures of which are hereby incorporated by reference.

FIELD OF THE INVENTION

The present invention relates to a process for the large scale preparation of an $A_{2A}$-adenosine receptor agonist, and also relates to polymorphs of that compound, and to methods of isolating a specific polymorph.

BACKGROUND

Adenosine is a naturally occurring nucleoside, which exerts its biological effects by interacting with a family of adenosine receptors known as $A_1$, $A_{2A}$, $A_{2B}$, and $A_3$, all of which modulate important physiological processes. One of the biological effects of adenosine is to act as a coronary vasodilator; this result being produced by interaction with the $A_{2A}$ adenosine receptor. This effect of adenosine has been found to be useful as an aid to imaging of the heart, where coronary arteries are dilated prior to administration of an imaging agent (for example thallium 201), and thus, by observation of the images thus produced, the presence or absence of coronary artery disease can be determined. The advantage of such a technique is that it avoids the more traditional method of inducing coronary vasodilation by exercise on a treadmill, which is clearly undesirable for a patient that has a coronary disease.

However, administration of adenosine has several disadvantages. Adenosine has a very short half life in humans (less than 10 seconds), and also has all of the effects associated with $A_1$, $A_{2A}$, $A_{2B}$, and $A_3$ receptor agonism. Thus the use of a selective $A_{2A}$ adenosine receptor agonist would provide a superior method of producing coronary vasodilation, particularly one with a longer half life and few or no side effects.

A class of compounds possessing these desirable properties was disclosed in U.S. Pat. No. 6,403,567, the complete disclosure of which is hereby incorporated by reference. In particular, one compound disclosed in this patent, (1-{9-[(4S,2R,3R,5R)-3,4-dihydroxy-5-(hydroxymethyl)oxolan-2-yl]-6-aminopurin-2-yl}pyrazol-4-yl)-N-methylcarboxamide, has been shown to be a highly selective $A_{2A}$-adenosine receptor agonist, and is presently undergoing clinical trials as a coronary vasodilator useful in cardiac imaging.

Given the heightened interest in this and similar compounds, it has become desirable to find new methods of synthesis that provide a convenient method for making large quantities of the material in good yield and high purity. The patent that discloses the compound of interest (U.S. Pat. No. 6,403,567) provides several methods for preparing the compound. However, although these methods are suited to small scale syntheses, all synthetic methods disclosed in the patent utilize protecting groups, which is undesirable for large scale syntheses.

Additionally, it was discovered that the desired product (that is (1-{9-[(4S,2R,3R,5R)-3,4-dihydroxy-5-(hydroxymethyl)oxolan-2-yl]-6-aminopurin-2-yl}pyrazol-4-yl)-N-methylcarboxamide) is capable of existing in at least three different crystalline forms, the most stable of which is a monohydrate. This polymorph is stable under relative humidity stress conditions, up to its melting point. Accordingly, it is desirable that the final product produced in the new syntheses is obtained as the stable monohydrate.

SUMMARY OF THE INVENTION

Thus, it is an object of this invention to provide convenient syntheses for the large scale preparation of (1-{9-[(4S,2R,3R,5R)-3,4-dihydroxy-5-(hydroxymethyl)oxolan-2-yl]-6-aminopurin-2-yl}pyrazol-4-yl)-N-methylcarboxamide, and polymorphs thereof, preferably as its monohydrate. Accordingly, in a first aspect, the invention relates to the preparation of a compound of the Formula I:

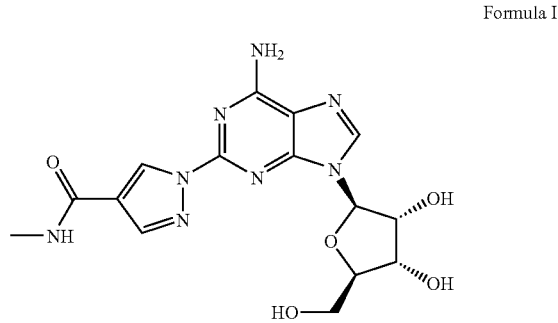

Formula I comprising:

contacting a compound of the formula (3):

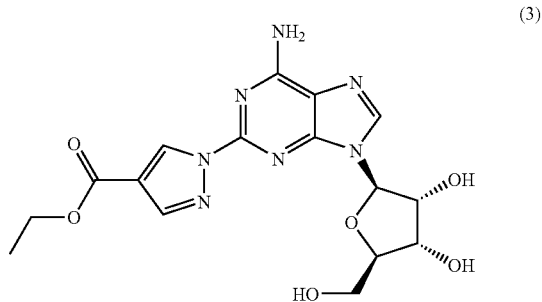

(3)

with methylamine.

In one embodiment the reaction is conducted in an aqueous solution of methylamine, initially at a temperature of about 0-5° C., followed by warming to about 50-70° C. Alternatively, the reaction is conducted as above but in a sealed pressure reactor.

In a second embodiment, the product is isolated as the pure monohydrate by dissolving the product in a solvent, for example dimethylsulfoxide, addition of purified water, filtering the slurry thus formed, washing the contents of the filter with water followed by ethanol, and drying the solid that remains under vacuum at a temperature that does not exceed 40° C.

In a second aspect, the invention relates to the preparation of a compound of the formula (3):

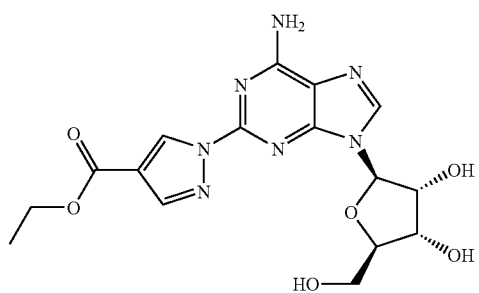
(3)

comprising:

contacting a compound of the formula (2):

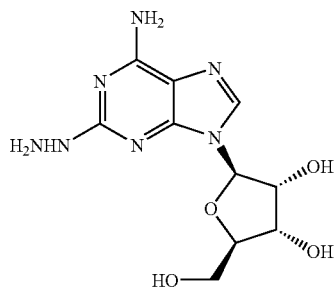

with ethyl 2-formyl-3-oxopropionate.

In one embodiment, the reaction is conducted in ethanol, at a temperature of about 80° C., with about 1.1 molar equivalents of ethyl 2-formyl-3-oxopropionate.

In a third aspect, the invention relates to the preparation of a compound of the formula (2):

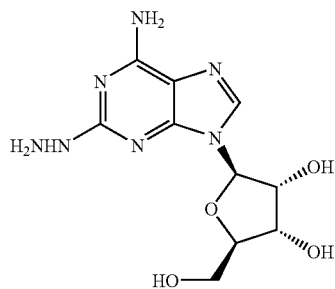
(2)

comprising:

contacting a compound of the formula (1):

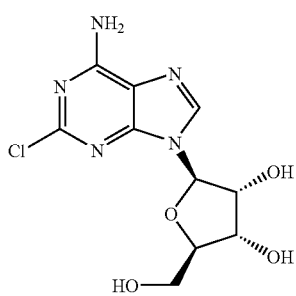
(1)

with hydrazine.

The above described synthesis is suitable for the large scale synthesis of the desired product, which is provided in good yield, although one minor impurity is seen in the final product. This impurity has been shown to be unchanged intermediate of the formula (2); that is, the compound of the formula:

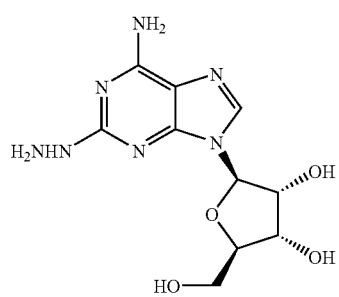
(2)

Although this impurity can be removed from the final product by crystallization, it was decided to seek an alternative synthesis that had all of the advantages of the above synthesis but did not give the compound of formula (2) as an impurity in the final product.

Thus, in a fourth aspect, the invention relates to a method of synthesizing (1-{9-[(4S,2R,3R,5R)-3,4-dihydroxy-5-(hydroxymethyl)oxolan-2-yl]-6-aminopurin-2-yl}pyrazol-4-yl)-N-methylcarboxamide by contacting a compound of the formula (4):

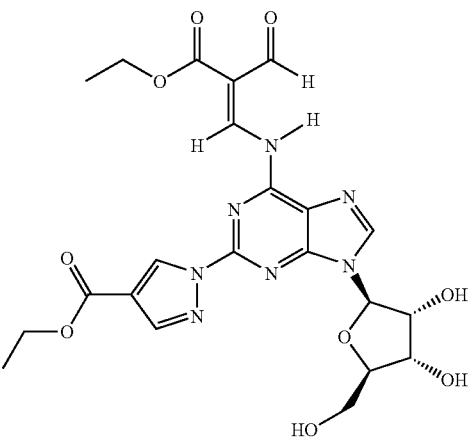
(4)

with methylamine.

In one embodiment the reaction is conducted in an aqueous solution of methylamine, initially at a temperature of about 0-5° C., followed by warming to about 50-70° C. Preferably, the reaction is conducted in a sealed pressure reactor.

In a second embodiment, the product is isolated as the pure monohydrate by dissolving the product in a solvent, for example dimethylsulfoxide, addition of purified water, filtering the slurry thus formed, washing the contents of the filter with water followed by ethanol, and drying the solid that remains under vacuum at a temperature that does not exceed 40° C.

In a fifth aspect, the invention relates to a method of synthesizing a compound of the formula (4):

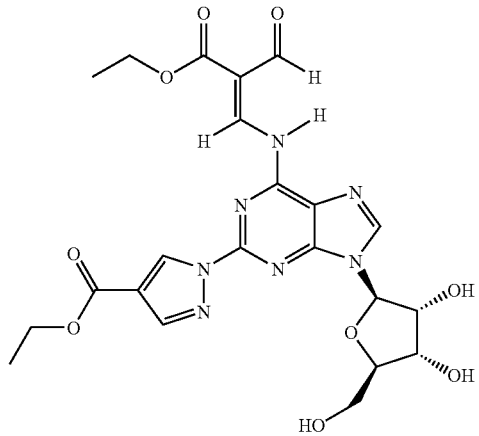

(4)

comprising contacting a compound of the formula (2):

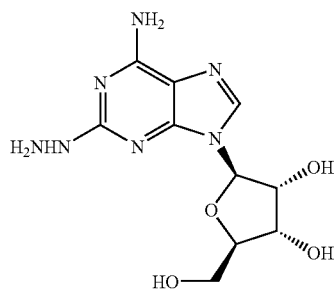

(2)

with an excess of ethyl 2-formyl-3-oxopropionate, preferably about a 2-10 fold excess, more preferably about a 5-10 fold excess.

In one embodiment, the reaction is conducted in ethanol, at a temperature of about 80° C. The ethyl 2-formyl-3-oxopropionate is present in a 5-10 fold excess.

DEFINITIONS AND GENERAL PARAMETERS

As used in the present specification, the following words and phrases are generally intended to have the meanings as set forth below, except to the extent that the context in which they are used indicates otherwise.

"Optional" or "optionally" means that the subsequently described event or circumstance may or may not occur, and that the description includes instances where said event or circumstance occurs and instances in which it does not.

The term "therapeutically effective amount" refers to that amount of a compound of Formula I that is sufficient to effect treatment, as defined below, when administered to a mammal in need of such treatment. The therapeutically effective amount will vary depending upon the subject and disease condition being treated, the weight and age of the subject, the severity of the disease condition, the manner of administration and the like, which can readily be determined by one of ordinary skill in the art.

The term "treatment" or "treating" means any treatment of a disease in a mammal, including:
  (i) preventing the disease, that is, causing the clinical symptoms of the disease not to develop;
  (ii) inhibiting the disease, that is, arresting the development of clinical symptoms; and/or
  (iii) relieving the disease, that is, causing the regression of clinical symptoms.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

The term "polymorph" is intended to include amorphous and solvates of (1-{9-[(4S,2R,3R,5R)-3,4-dihydroxy-5-(hydroxymethyl)oxolan-2-yl]-6-aminopurin-2-yl}pyrazol-4-yl)-N-methylcarboxamide.

It has been discovered that this compound is capable of existing in at least three different crystalline forms, referred to herein as Form A, Form B, Form C, and an amorphous product.

Form A: This polymorph can be produced by crystallizing 1-{9-[(4S,2R,3R,5R)-3,4-dihydroxy-5-(hydroxymethyl)oxolan-2-yl]-6-aminopurin-2-yl}pyrazol-4-yl)-N-methylcarboxamide from protic solvents, for example ethanol or ethanol/water mixtures, or from a polar solvent, for example dimethylsulfoxide/water. Form A has been shown to be a monohydrate, and is the most stable of the various polymorphs at ambient temperatures. It is stable under relative humidity stress conditions up to its melting point.

Figure 4:
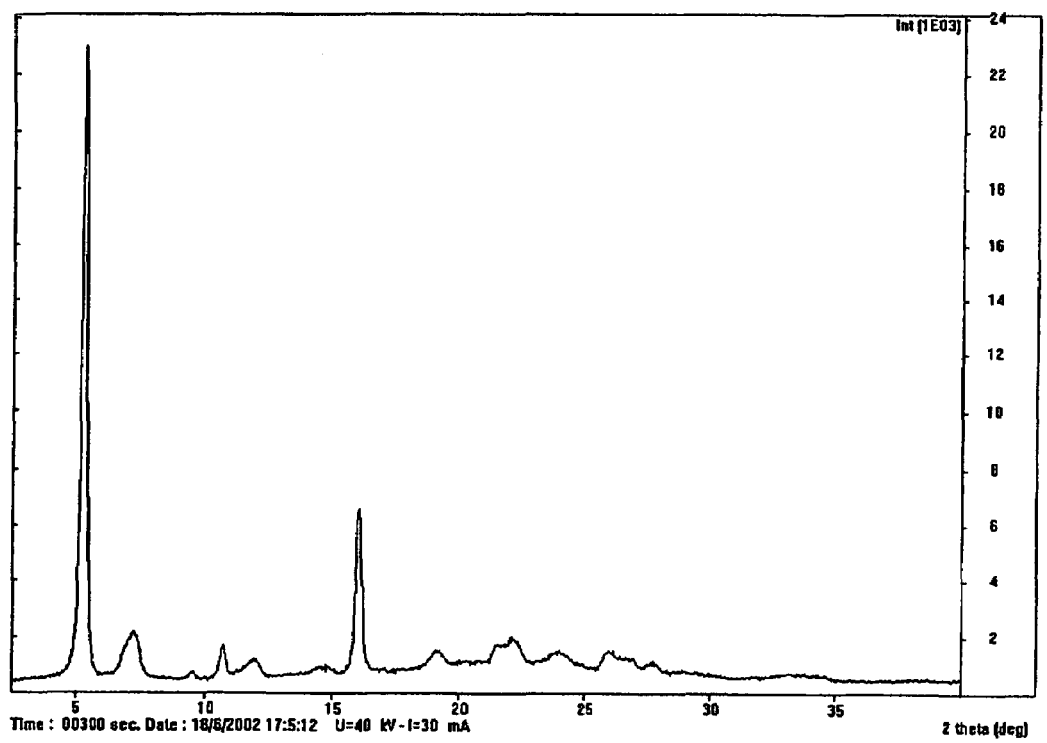
FIG. 4 shows the X-Ray diffraction pattern for (1-{9-[(4S,2R,3R,5R)-3,4-dihydroxy-5-(hydroxymethyl)oxolan-2-yl]-6-aminopurin-2-yl}pyrazol-4-yl)-N-methylcarboxamide Form B.

Form B: This polymorph is produced by evaporating under vacuum a solution of 1-{9-[(4S,2R,3R,5R)-3,4-dihydroxy-5-(hydroxymethyl)oxolan-2-yl]-6-aminopurin-2-yl}pyrazol-4-yl)-N-methylcarboxamide in trifluoroethanol at ambient temperatures. The X-ray analysis of the crystals was distinctly different from any other polymorph (see FIG. 4), but it was difficult to determine its constitution, as the X-ray analysis gave disordered broad peaks, and the polymorph contained varying amounts of water. It was found to be difficult to reliably reproduce the preparation of this polymorph.

Figure 5:
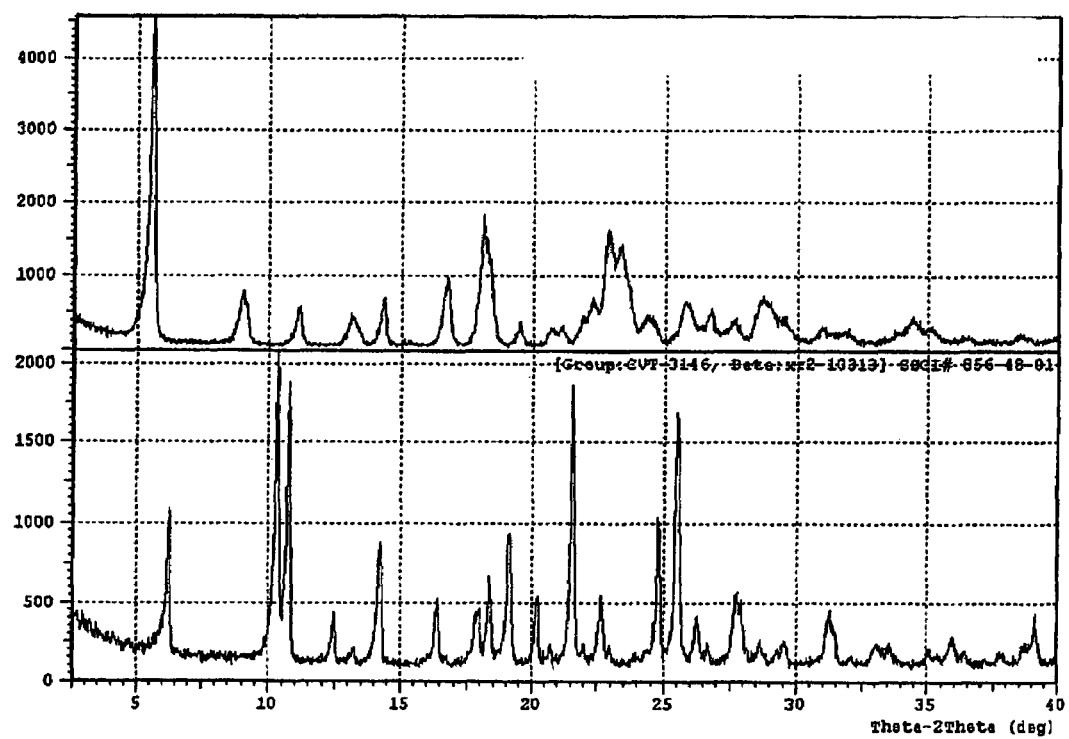
FIG. 5 shows the X-Ray diffraction pattern for (1-{9-[(4S,2R,3R,5R)-3,4-dihydroxy-5-(hydroxymethyl)oxolan-2-yl]-6-aminopurin-2-yl}pyrazol-4-yl)-N-methylcarboxamide Form C as compared to Form A.

Form C: This polymorph is produced by slurrying 1-{9-[(4S,2R,3R,5R)-3,4-dihydroxy-5-(hydroxymethyl)oxolan-2-yl]-6-aminopurin-2-yl}pyrazol-4-yl)-N-methylcarboxamide in acetonitrile for a long period of time at 60° C. The X-ray analysis of the crystals was distinctly different from any other polymorph (see FIG. 5). Polymorph C was shown to be a variable hydrate, which, at elevated temperatures, desolvates to an unstable form.

Amorphous Material: This polymorph is produced by heating Form A polymorph at a temperature of up to 200° C. This polymorph is unstable in the presence of atmospheric moisture, forming variable hydrates.

Techniques for Analysis of Forms A, B, C and Amorpheous Material

X-Ray Powder Diffraction

X-ray powder diffraction (XRPD) analyses were carried out on a Shimadzu XRD-6000 X-ray powder diffractometer using Cu Kα radiation. The instrument was equipped with a fine focus X-ray tube, and the tube voltage and amperage were set to 40 kV and 40 mA respectively. The divergence and scattering slits were set at 1" and the receiving slit was set at 0.15 mm. Diffracted radiation was detected by a NaI scintillation detector. A theta-two theta continuous scan at 3°/min (0.4 sec/0.02° step) from 2.5-40° 2θ was used. A silicon standard was used to check the instrument alignment. Data were collected and analyzed using XRD-6000 v. 4.1 software.

X-ray powder diffraction (XRPD) analyses were also performed using an Inel XRG-3000 diffractometer equipped with a CPS (Curved Position Sensitive) detector with a 2θ range of 120°. The instrument calibration was performed using a silicon reference standard. The tube voltage and amperage were set to 40 kV and 30 mA, respectively. The monochromator slit was set at 5 mm by 80 μm. Samples were placed in an aluminum sample holder with a silicon insert or in glass XRPD-quality capillaries. Each capillary was mounted onto a goniometer head that is motorized to permit spinning of the capillary during data acquisition. Real time data were collected using Cu-Kα radiation at a resolution of 0.03° 2θ. Typically, data were collected over a period of 300 seconds. Only the data points within the range of 2.5-40° 2θ are displayed in the plotted XRPD patterns.

Thermal Analyses

Thermogravimetric (TG) analyses were carried out on a TA Instruments 2050 or 2950 thermogravimetric analyzer. The calibration standards were nickel and Alumel™. Samples were placed in an aluminum sample pan, inserted into the TG furnace, and accurately weighed. The samples were heated in nitrogen at a rate of 10° C./min to either 300 or 350° C. Unless stated otherwise, samples weights were equilibrated at 25° C. in the TGA furnace prior to analysis.

Differential scanning calorimetry (DSC) analyses were carried out on a TA Instruments differential scanning calorimeter 2920. Accurately weighed samples were placed in either crimped pans or hermetically sealed pans that contained a pinhole to allow for pressure release. Each sample was heated under nitrogen at a rate of 10° C./min to either 300 or 350° C. Indium metal was used as the calibration standard. Temperatures were reported at the transition maxima.

Infrared Spectroscopy

Infrared spectra were acquired on Magna 860® Fourier transform infrared (FT-IR) spectrophotometer (Nicolet Instrument Corp.) equipped with an Ever-Glo mid/far IR source, an extended range potassium bromide beamsplitter, and a deuterated triglycine sulfate (DTGS) detector. Unless stated otherwise, a Spectra-Tech, Inc. diffuse reflectance accessory (the Collector™) was used for sampling. Each spectrum represents 256 co-added scans at a spectral resolution of 4 cm$^{-1}$. Sample preparation for the compound consisted of placing the sample into a microcup and leveling the material with a frosted glass slide. A background data set was acquired with an alignment mirror in place. The spectra represent a ratio of the sample single-beam data set to the background single beam data set. Wavelength calibration of the instrument was performed using polystyrene.

NMR Spectroscopy

Solution phase $^1$H NMR spectra of the were acquired at ambient temperature on a Bruker model AM-250 spectrometer operating at 5.87 T (Larmor frequency: $^1$H=250 MHz). Time-domain data were acquired using a pulse width of 7.5 ps and an acquisition time of 1.6834 second over a spectral window of 5000 Hz. A total of 16,384 data points were collected. A relaxation delay time of 5 seconds was employed between transients. Each data set typically consisted of 128 coaveraged transients. The spectra were processed utilizing GRAMS 132 A1 software, version 6.00. The free induction decay (FID) was zero-filled to four times the number of data points and exponentially multiplied with a line-broadening factor of 0.61 Hz prior to Fourier transformation. The $^1$H spectra were internally referenced to tetramethylsilane (0 ppm) that was added as an internal standard.

Alternatively, NMR analysis was carried out as described in Example 4.

Moisture Sorption/Desorption Analyses

Moisture sorption/desorption data were collected on a VTI SGA-100 Vapor Sorption Analyzer. Sorption and desorption data were collected over a range of 5% to 95% relative humidity (RK) at 10% RH intervals under a nitrogen purge. Sodium chloride (NaCl) and polyvinylpyrrolidone (PVP) were used as the calibration standards. Equilibrium criteria used for analysis were less than 0.0100% weight change in 5 minutes, with a maximum equilibration time of 180 minutes if the weight criterion was not met. The plotted data have not been corrected for the initial moisture content.

Nomenclature

The structure of the compound (1-{9-[(4S,2R,3R,5R)-3,4-dihydroxy-5-(hydroxymethyl)oxolan-2-yl]-6-aminopurin-2-yl}pyrazol-4-yl)-N-methylcarboxamide is as follows:

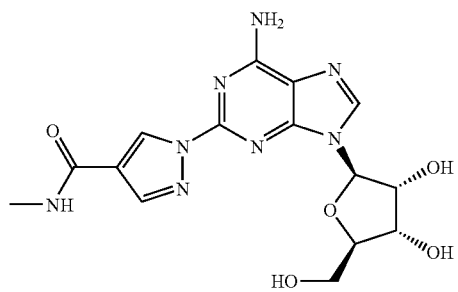

Synthesis of (1-{9-[(4S,2R,3R,5R)-3,4-dihydroxy-5-(hydroxymethyl)oxolan-2-yl]-6-aminopurin-2-yl}pyrazol-4-yl)-N-methylcarboxamide One method for the large scale synthesis of (1-{9-[(4S,2R,3R,5R)-3,4-dihydroxy-5-(hydroxymethyl)oxolan-2-yl]-6-aminopurin-2-yl}pyrazol-4-yl)-N-methylcarboxamide is shown in Reaction Scheme I.

REACTION SCHEME I

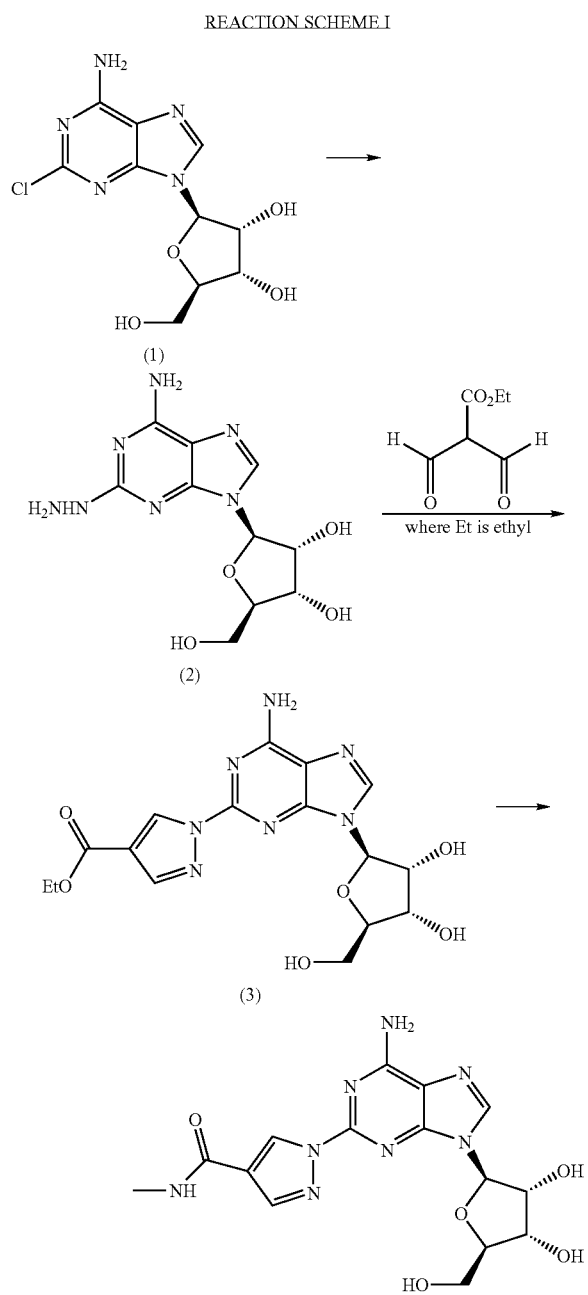

Step 1—Preparation of Formula (2)

The compound of formula (2) is prepared from the compound of formula (1) by reaction with hydrazine monohydrate in the absence of a solvent. The reaction is conducted at a temperature of about 40° C. plus/minus 5° C. When the reaction is complete, the product of formula (2) is isolated by stirring with a protic solvent in which the compound of formula (2) has limited solubility, for example ethanol or isopropanol. The mixture is stirred for about 1-5 hours, and then filtered. The solid is purified by stirring with water, filtering, and washing with water followed by isopropanol and dried under vacuum, which is taken to the next step without purification.

Step 2—Preparation of Formula (3)

The compound of formula (2) is then converted to a compound of formula (3) by reacting with about 1-1.2 molar equivalents of ethyl 2-formyl-3-oxopropionate. The reaction is conducted in a protic solvent, preferably ethanol, at about reflux temperature, for about 2-4 hours. After cooling, to about 0° C., the solid is filtered off, washed with cold ethanol, and dried under reduced pressure. The product of formula (3) is taken to the next step without purification.

Step 3—Preparation of Final Product

The final product is prepared from the compound of formula (3) by reacting with methylamine, preferably aqueous methylamine. The reaction is carried out at about room temperature, for about 4 hours. The product of Formula I is isolated by conventional means, for example by filtration, washing the solid with cold ethanol, and drying under reduced pressure.

Preparation of Starting Materials (4S,2R,3R,5R)-2-(6-amino-2-chloropurin-9-yl)-5-(hydroxymethyl)oxolane-3,4-diol is used as a starting material in step 1. This compound is commercially available.

Ethyl 2-formyl-3-oxopropanoate is used as a starting material in step 2. It is commercially available, or may be made as shown in Reaction Scheme II.

REACTION SCHEME II

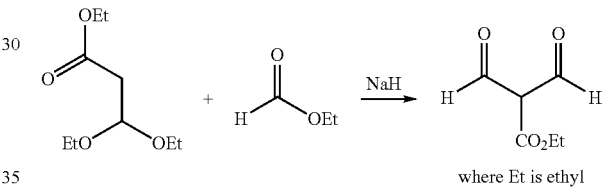

Ethyl 3,3-diethoxypropionate is reacted with ethyl formate in the presence of a strong base, preferably sodium hydride. The reaction is carried out at about 0-5° C., for about 24 hours. The product is isolated by conventional means, for example by the addition of water and extraction of impurities with a conventional solvent, for example t-butylmethyl ether, acidification of the aqueous phase with, for example, hydrochloric acid, followed by extraction with a solvent such as dichloromethane, and removing the solvent from the dried extract under reduced pressure.

A preferred method for the large scale synthesis of (1-{9-[(4S,2R,3R,5R)-3,4-dihydroxy-5-(hydroxymethyl)oxolan-2-yl]-6-aminopurin-2-yl}pyrazol-4-yl)-N-methylcarboxamide is shown in Reaction Scheme III.

REACTION SCHEME III

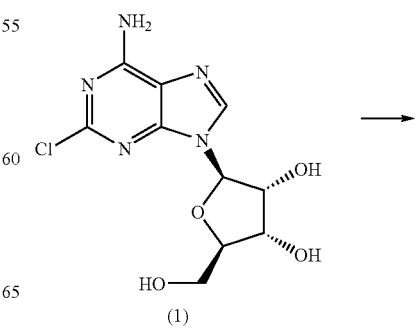

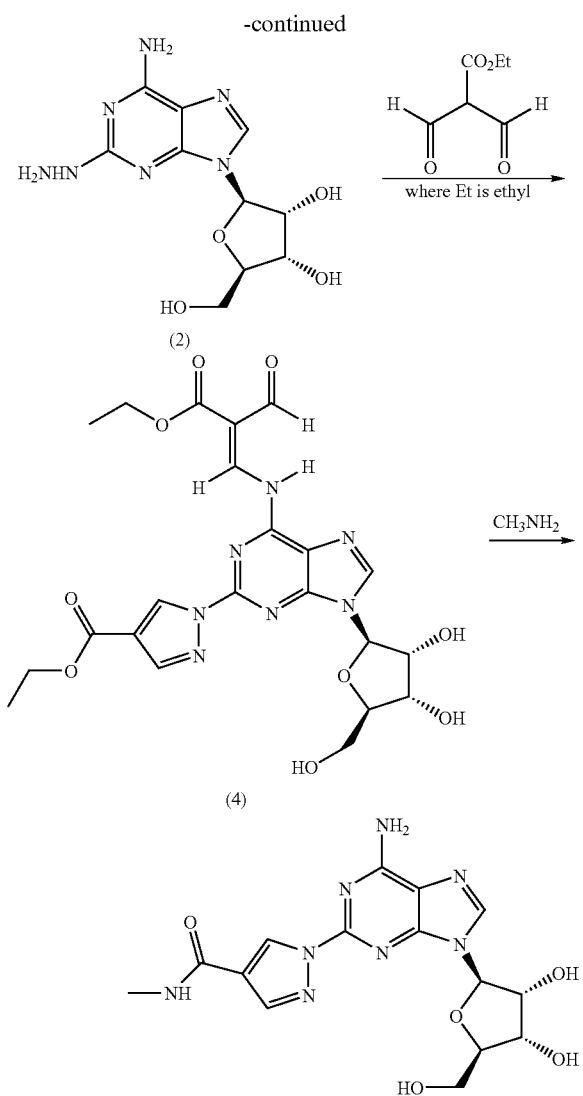

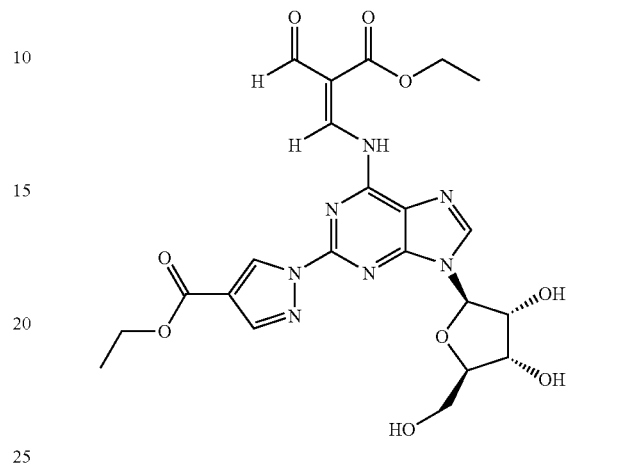

The compound of formula (4) is drawn as a (2E) alkene derivative, as this is the major isomer formed in this reaction. However, it should be noted that a significant amount of the (2Z) alkene derivative may also be formed in this reaction; that is:

named as ethyl (2Z)-3-({9-[(4S,2R,3R,5R)-3,4-dihydroxy-5-(hydroxymethyl)-oxolan-2-yl]-2-[4-(ethoxycarbonyl) pyrazolyl]purin-6-yl} amino)-2-formylprop-2-enoate.

Accordingly, although the compound of formula (4) is represented as the (2E) alkene derivative only, the term "compound of formula (4)" is intended to include both the instance where it is solely the (2E) isomer, and the instance where the major portion of the product is the (2E) isomer and a minor portion of the (2Z) isomer is also present. The conversion of the compound of formula (4) to the final product by reaction with methylamine as described in Step 3 proceeds in the same manner whether the compound of formula (4) is present as the (2E) isomer or as a mixture of the (2E) isomer and the (2Z) isomer.

Step 1—Preparation of Formula (2)

The compound of formula (2) is prepared from the compound of formula (1) by reaction with hydrazine monohydrate in the absence of a solvent. The reaction is conducted at a temperature of about 45-55° C. plus/minus 5° C. When the reaction is complete, the product of formula (2) is isolated by stirring with a protic solvent in which the compound of formula (2) has limited solubility, for example ethanol or isopropanol. The mixture is stirred for about 1-5 hours, and then filtered. The solid is purified by stirring with water, filtering, and washing with water followed by ethanol or isopropanol and dried under vacuum, which is taken to the next step without purification.

Step 2—Preparation of Formula (4)

The compound of formula (2) is then converted to a compound of formula (4) by reacting with an excess of ethyl 2-formyl-3-oxopropionate, for example a 2-10 fold excess, preferably about 5-10 fold excess. The reaction is conducted in a protic solvent, for example ethanol, at about reflux temperature, for about 2-4 hours. After cooling, to about 0° C., the solid is filtered off, washed with cold ethanol, and dried under reduced pressure, and the product of formula (4) is taken to the next step without purification.

Step 3—Preparation of Final Product

The final product is prepared from the compound of formula (4) by reacting with methylamine, preferably aqueous methylamine. The reaction is initially carried out at about 0-5° C. for about 8 hours, preferably in a pressure reactor, followed by raising the temperature to 50-60° C. over about 1 hour, and maintaining the temperature for 15-30 minutes. The product is isolated by conventional means, for example by cooling to 0-5° C. and maintaining a vacuum for about 1 hour, thus removing the methylamine. The vacuum is removed, and the remaining contents held at 0-5° C. for at least 30 minutes, followed by filtration. The solid thus obtained is washed with water followed by ethanol, and dried under reduced pressure.

This process provides (1-{9-[(4S,2R,3R,5R)-3,4-dihydroxy-5-(hydroxymethyl)oxolan-2-yl]-6-aminopurin-2-yl}pyrazol-4-yl)-N-methylcarboxamide as its monohydrate. This polymorph can be further purified by dissolving in dimethylsulfoxide, filtering any solid impurities from the solution, and precipitating the monohydrate from solution by addition of water.

EXAMPLE 1

Preparation of Ethyl-2-formyl-3-oxopropionate

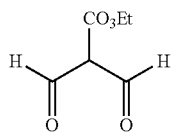

A three- or four-neck round bottom flask equipped with magnetic stir bar, thermocouple, digital thermometer, gas inlet and outlet and addition funnel was flushed with argon. Ethyl 3,3-diethoxypropionate (64.5 g) in tetrahydrofuran were charged to the addition funnel. Sodium hydride (21.2 g of a 60% dispersion) was charged to the reaction flask followed by tetrahydrofuran. The contents of the flask were cooled to 0-5° C. in an ice-bath, and ethyl formate (257 g) was added. The mixture was cooled to 0-5° C. and the contents of the addition funnel added dropwise, maintaining an internal temperature of less than 5° C. The ice-bath was removed and the contents allowed to warm to ambient temperature. Consumption of ethyl 3,3-diethoxypropionate was monitored by TLC analysis. The reaction was quenched by addition of ice-water (10.6 vol), and extracted three times with methyl t-butyl ether (5.4 vol each), and the organic layers discarded. The aqueous phase was acidified with conc. hydrochloric acid to a pH of 1 to 1.5. The acidified aqueous layer was extracted three times with dichloromethane and the combined organic layers dried over sodium sulfate. The solvent was removed under reduced pressure, and the residue distilled under vacuum, to provide ethyl 2-formyl-3-oxopropionate, 27.92 g, 70% yield.

EXAMPLE 2

A. Preparation of 2-Hydrazinoadenosine (2)

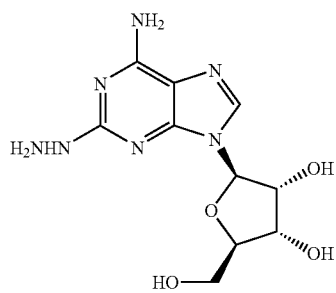

A flask equipped with a mechanical stirrer, gas inlet, gas outlet and thermocouple was flushed with argon. 2-Chloroadenosine hemihydrate (53.1 g) was added, followed by hydrazine monohydrate (134 g). The mixture was stirred while heating to 40-45° C. for 2 hours. The progress of the reaction was followed by TLC analysis. When the reaction was complete, the heat source was removed and ethanol (800 ml) was added. The mixture was stirred for 2 hours at ambient temperature, then the precipitate collected by filtration. The filter cake was washed with ethanol and dried under reduced pressure for 30 minutes. The solids were transferred to a clean flask equipped with a mechanical stirrer and water (300 ml) was added. The suspension was stirred at room temperature for 18 hours, and the solids isolated by filtration. The filter cake was washed with ice-cold water (300 ml) followed by a wash with ice-cold ethanol (300 ml). The solid was dried under reduced pressure to provide 2-hydrazinoadenosine (41.38 g, 81.4% yield, 99.3% purity).

B. Alternative Preparation of 2-Hydrazinoadenosine (2)

A reaction vessel containing hydrazine hydrate (258 g, 250 ml) was heated to 40-50° C. To the warm mixture 2-chloroadenosine hemihydrate (100 g) was added in portions, maintaining the temperature between 45-55° C. The temperature was kept at this temperature for two hours, and then deionized water (500 ml) was added over a period of 30 minutes, maintaining the temperature at 45-55° C. The mixture was then gradually cooled to 0-5° C. over a period of 3 hours, then stirred at this temperature for a further 30 minutes. The solid was then filtered off, and washed with cold (2-5° C.) deionized water (200 ml), followed by ethanol (400 ml). The solid was dried under vacuum for 12 hours, to provide 2-hydrazinoadenosine.

EXAMPLE 3

Preparation of Ethyl 1-{9-[(4S,2R,3R,5R)-3,4-dihydroxy-5-(hydroxymethyl)oxolan-2-yl]-6-aminopurin-2-yl}pyrazole-4-carboxylate (3)

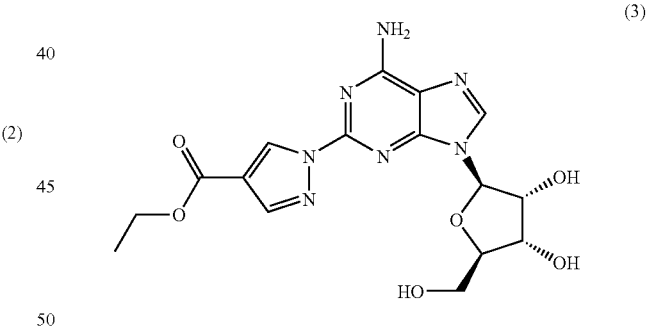

Ethyl 2-formyl-3-oxopropionate (23.93 g, 0.17 mol) was placed in a flask equipped with mechanical stirrer, gas inlet, gas outlet and reflux condenser. 2-Propanol was added to the flask followed by 2-hydrazinoadenosine (44.45 g, 0.15 mol). The mixture was heated to reflux under stirring for 2-4 hours, following the progress of the reaction by TLC analysis. When the reaction was judged complete, the heat source was removed and the mixture cooled to room temperature. The suspension was cooled under stirring in an ice-bath for 1.5 to 2 hours. The solids were isolated by vacuum filtration, and washed with ice-cold 2-propanol. The product, ethyl 1-{9-[(4S,2R,3R,5R)-3,4-dihydroxy-5-(hydroxymethyl)oxolan-2-yl]-6-aminopurin-2-yl}pyrazole-4-carboxylate, was dried under reduced pressure to a constant weight. Yield 54.29 g, purity (by HPLC) 96.6%.

EXAMPLE 4

Preparation of (1-{9-[(4S,2R,3R,5R)-3,4-dihydroxy-5-(hydroxymethyl)oxolan-2-yl]-6-aminopurin-2-yl}pyrazol-4-yl)-N-methylcarboxamide

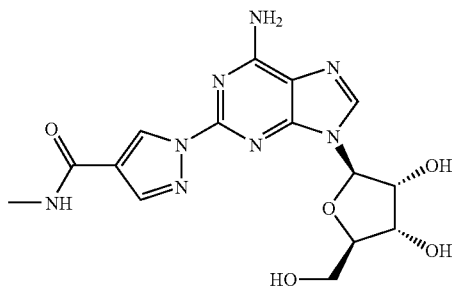

A mixture of ethyl 1-{9-[(4S,2R,3R,5R)-3,4-dihydroxy-5-(hydroxymethyl)oxolan-2-yl]-6-aminopurin-2-yl}pyrazole-4-carboxylate (46.4 g) and methylamine (40% in water, 600 ml) was stirred at ambient temperature for about 4 hours, following the progress of the reaction by HPLC analysis. The majority of the excess methylamine was removed under reduced pressure, and the remaining mixture cooled at 0° C. for 2 hours. The solid material was filtered off, washed with ice-cold 200 proof ethanol, and dried under reduced pressure, to provide (1-{9-[(4S,2R,3R,5R)-3,4-dihydroxy-5-(hydroxymethyl)oxolan-2-yl]-6-aminopurin-2-yl}pyrazol-4-yl)-N-methylcarboxamide as its monohydrate, 36.6 g, purity 99.6%.

Figure 1:
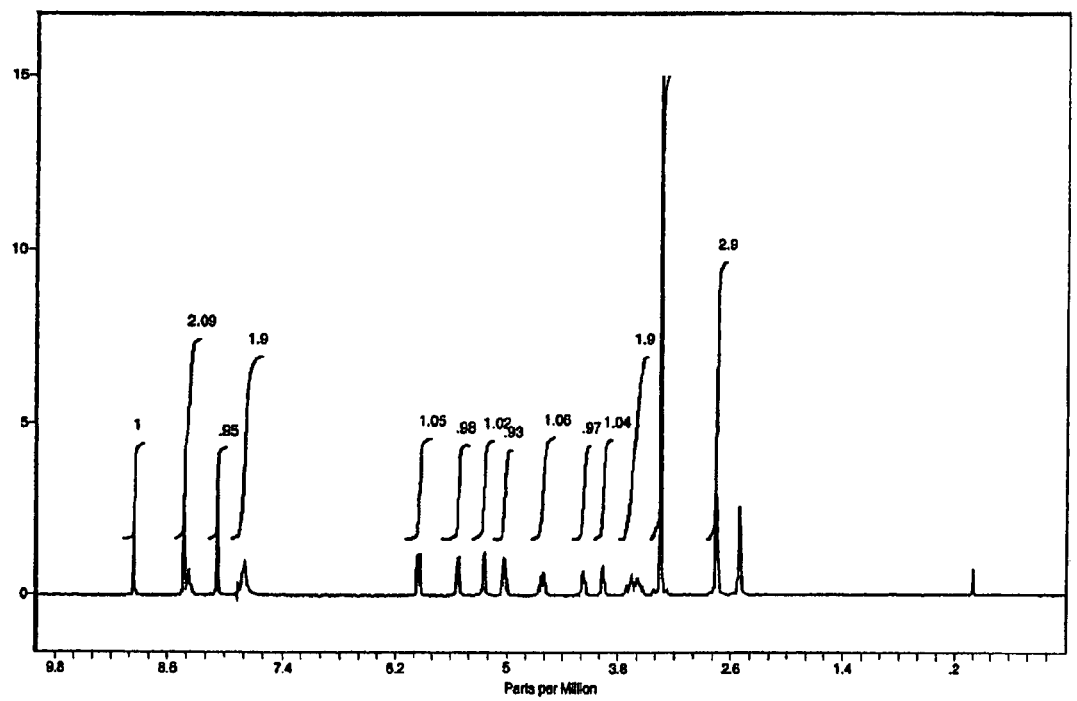
FIG. 1 is a $^1$H NMR spectrum of (1-{9-[(4S,2R,3R,5R)-3,4-dihydroxy-5-(hydroxymethyl)oxolan-2-yl]-6-aminopurin-2-yl}pyrazol-4-yl)-N-methylcarboxamide monohydrate (Form A).
Figure 2:
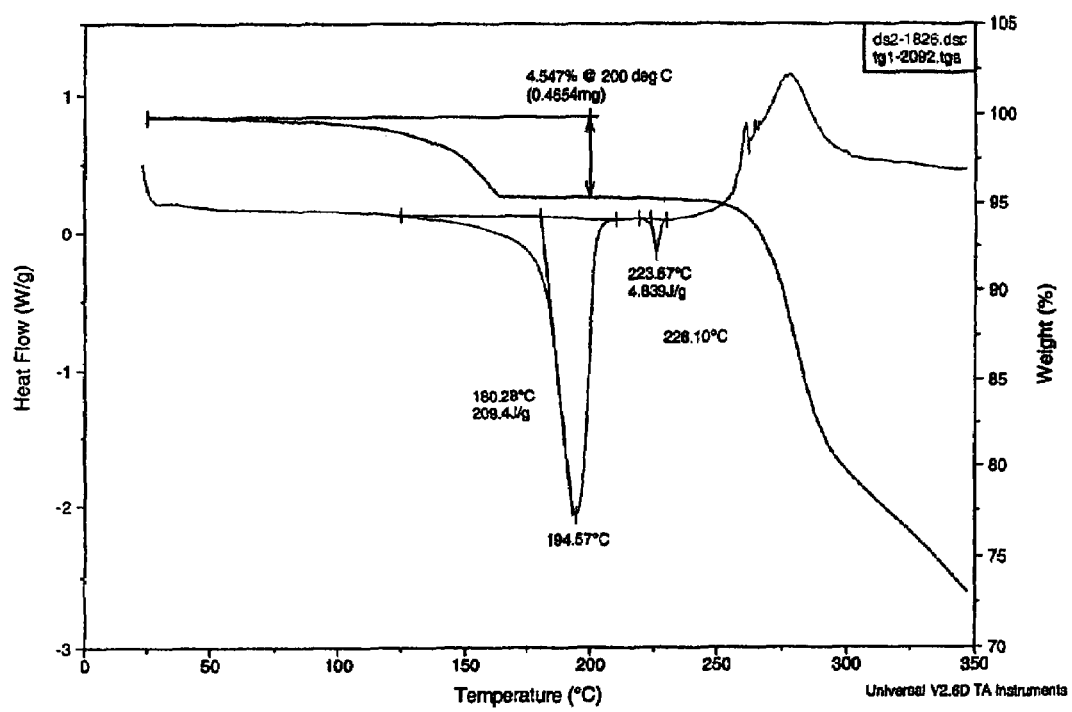
FIG. 2 shows the thermal analysis of (1-{9-[(4S,2R,3R,5R)-3,4-dihydroxy-5-(hydroxymethyl)oxolan-2-yl]-6-aminopurin-2-yl}pyrazol-4-yl)-N-methylcarboxamide monohydrate.
Figure 3:
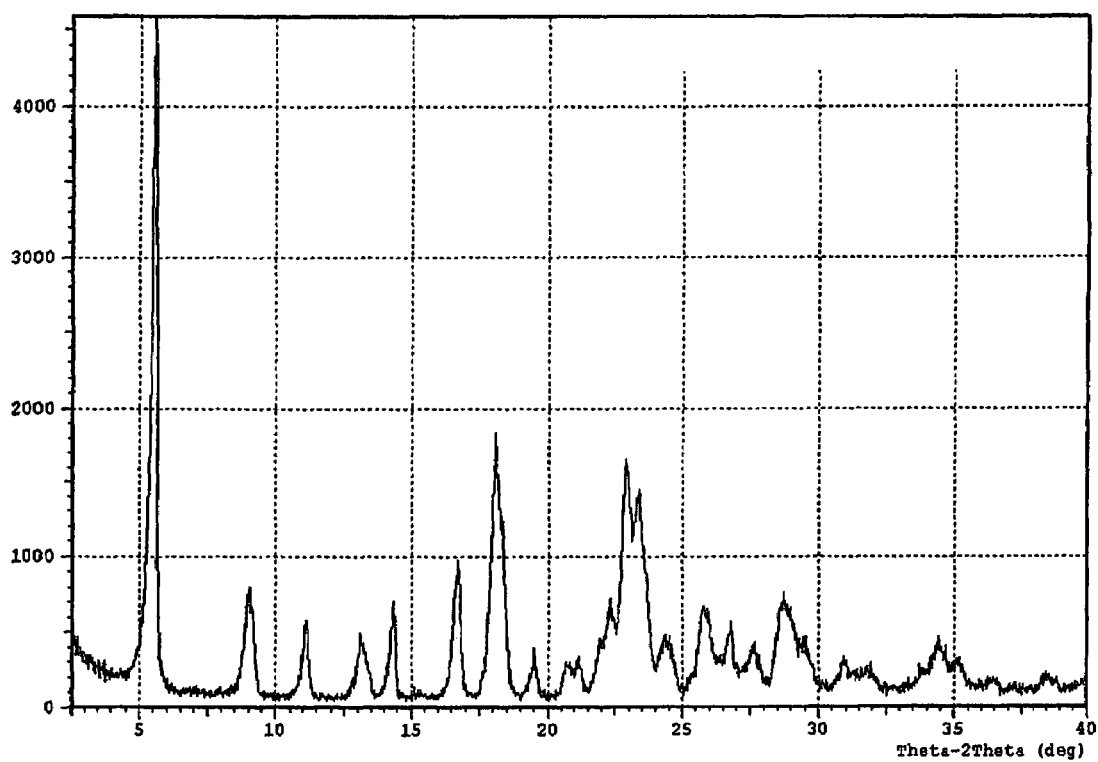
FIG. 3 shows the X-Ray diffraction pattern for (1-{9-[(4S,2R,3R,5R)-3,4-dihydroxy-5-(hydroxymethyl)oxolan-2-yl]-6-aminopurin-2-yl}pyrazol-4-yl)-N-methylcarboxamide monohydrate.

The structure of the material was confirmed by $^1$H NMR (see FIG. 1 and below). Thermal analysis (see FIG. 2) provided results consistent with the presence of one molecule of water. X-Ray powder diffraction patterns were obtained (FIG. 3)

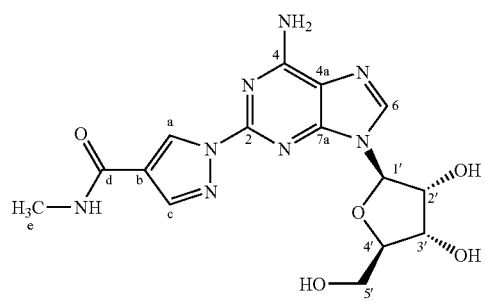

$^1$H and $^{13}$C NMR spectra were obtained in the following manner. Two samples of the material obtained above were weighed out and dissolved in d$_6$-DMSO-5.3 mg was used for the $^1$H spectra, and 20.8 mg was used for $^{13}$C spectra. All spectra were acquired at ambient temperature on a JEOL Eclipse$^+$ 400 spectrometer operating at 400 MHz for $^1$H and 100 MHz for $^{13}$C.

| Label | $^{13}$C shift (ppm) | $^1$H shift (ppm) | Multiplicity, splitting (Hz) |
|---|---|---|---|
| 2 | 150.5 or 150.3 | — | |
| 4 | 156.4 | — | |
| 4a | 117.9 | — | |
| 6 | 140.0 | 8.41 | s |
| 7a | 150.5 or 150.3 | — | |
| 1' | 86.9 | 5.94 | D, 6.2 |
| 2' | 73.7 | 4.62 | m |
| 2'-OH | — | 5.50 | D, 6.2 |
| 3' | 70.5 | 4.17 | m |
| 3'-OH | — | 5.23 | D, 4.7 |
| 4' | 85.7 | 3.96 | m |
| 5' | 61.5 | 3.67, 3.57 | m |
| 5'-OH | — | 5.02 | D, 5.7 |
| A | 140.9 | 8.07 | D, 0.8 |
| B | 120.2 | — | |
| C | 129.6 | 8.95 | D, 0.8 |
| D | 161.7 | — | |
| E | 25.6 | 2.76 | D, 4.6 |
| NH$_2$ | — | 7.77 | br s |
| NH | — | 8.35 | Q, 4.6 |

Purification of (1-{9-[(4S,2R,3R,5R)-3,4-dihydroxy-5-(hydroxymethyl)oxolan-2-yl]-6-aminopurin-2-yl}pyrazol-4-yl)-N-methylcarboxamide monohydrate A solution of (1-{9-[(4S,2R,3R,5R)-3,4-dihydroxy-5-(hydroxymethyl)oxolan-2-yl]-6-aminopurin-2-yl}pyrazol-4-yl)-N-methylcarboxamide monohydrate (100 g) in dimethylsulfoxide (300 ml) was filtered through a 0.6 to 0.8 micron prefilter and a 0.2 micron filter to remove any solid impurities. The filtrate was then slowly added over a period of 1 hour to deionized water (1 liter) with stirring, and the slurry thus produced stirred for not less than 1 hour. The solid was filtered off, washed with deionized water (2×1 liter), and dried under vacuum for not less than 1 hour. The dried product was then slurried again with deionized water (1.5 liter) for not less than 2 hours, filtered off, and washed with deionized water (1 liter) followed by absolute ethanol (750 ml). The purified product was dried under vacuum at a temperature of not more than 40° C. for not less than 12 hours, to provide (1-{9-[(4S,2R,3R,5R)-3,4-dihydroxy-5-(hydroxymethyl)oxolan-2-yl]-6-aminopurin-2-yl}pyrazol-4-yl)-N-methylcarboxamide monohydrate free of any 2-hydrazinoadenosine impurity.

EXAMPLE 5

Preparation of Ethyl (2E)-3-({9-[(4S,2R,3R,5R)-3,4-dihydroxy-5-(hydroxymethyl)-oxolan-2-yl]-2-[4-(ethoxycarbonyl)pyrazolyl]purin-6-yl}amino)-2-formylprop-2-enoate

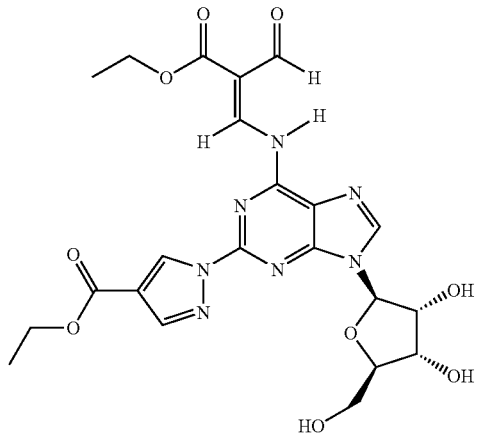

A mixture of 2-hydrazinoadenosine (100 g, 0.34 mol), ethyl 2-formyl-3-oxopropionate (242 g, 1.7 mol) and absolute ethanol were charged to a reactor, and the mixture heated to reflux for 2 hours. When the reaction was judged complete, the heat source was removed and the mixture gradually cooled to 5-10° C. over a period of 3 hours. The slurry was stirred for 30 minutes at this temperature, and the mixture filtered. The solid material was washed with cold (5-10° C.) absolute ethanol, and then dried under vacuum at a temperature that did not exceed 40° C., to provide ethyl (2E)-3-({9-[(4S,2R,3R,5R)-3,4-dihydroxy-5-(hydroxymethyl)oxolan-2-yl]-2-[4-(ethoxycarbonyl)-pyrazolyl]purin-6-yl}amino)-2-formylprop-2-enoate.

An elemental analysis gave the following results: C, 48.75%; H, 4.86%; N, 18.05%; O, 27.57. Theoretical: C, 49.72%; H, 4.74%; N, 18.45%; O, 27.09. The analysis corresponds within experimental error limits to the hemihydrate of the desired product. (C, 48.89%; H, 4.81%; N, 18.1%; O, 28.12)

$^1$H and $^{13}$C NMR spectra were obtained in the following manner. 20.2 mg of the compound of formula (4) was dissolved in ~0.75 ml of DMSO-d6, and the spectra obtained at ambient temperature on a JEOL ECX-400 NMR spectrometer operating at 400 MHz for $^1$H and 100 MHz for $^{13}$C. The chemical shifts were referenced to the DMSO solvent, 2.50 ppm for $^1$H and 39.5 ppm for $^{13}$C.

Results

The $^1$H and $^{13}$C chemical shifts are listed in Table 1. Two isomers in a ratio of ~60/30 were observed in both the $^1$H and the $^{13}$C spectra, labeled as major and minor in the table.

| Atom[a] | $^{13}$C Chemical Shift (ppm) | $^1$H Chemical Shift (ppm) | Multiplicity[b], Splitting (Hz) |
|---|---|---|---|
| 21 (major) | 192.4 | 9.96 | d, 3.6 |
| 21 (minor) | 187.6 | 9.83 | s |
| 22 (minor) | 167.1 | — | — |
| 22 (major) | 165.2 | — | — |

-continued

| Atom[a] | $^{13}$C Chemical Shift (ppm) | $^1$H Chemical Shift (ppm) | Multiplicity[b], Splitting (Hz) |
|---|---|---|---|
| 15 (minor) | 161.8 | — | — |
| 15 (major) | 161.7 | — | — |
| 6 (major) | 153.1 | — | — |
| 6 (minor) | 152.9 | — | — |
| 2 (minor) | 149.4 | — | — |
| 2 (major) | 149.3 | — | — |
| 19 (minor) | 148.0 | 9.22 | d, 13.0 |
| 4 (minor) | 147.9 | — | — |
| 4 (major) | 147.8 | — | — |
| 19 (major) | 147.5 | 9.26 | d, 12.4, d, 3.6 |
| 8 (major) | 144.9 | 8.87 | s |
| 8 (minor) | 144.7 | 8.85 | s |
| 12 | 143.1 | 8.20-8.23 | m |
| 14 (minor) | 132.8 | 9.20 | d, ~0.7 |
| 14 (major) | 132.6 | 9.12 | d, ~0.7 |
| 5 (major) | 120.7 | — | — |
| 5 (minor) | 120.6 | — | — |
| 13 | 116.7 | — | — |
| 20 (minor) | 107.2 | — | — |
| 20 (major) | 106.1 | — | — |
| 1' (major) | 87.9 | 6.07 | d, 5.3 |
| 1' (minor) | 87.9 | 6.06 | d, 5.3 |
| 4' | 85.8 | 4.02 | q, 3.9 |
| 2' (minor) | 74.1 | 4.62 | q, ~5.4 |
| 2' (major) | 74.1 | 4.61 | q, ~5.4 |
| 3' | 70.1 | 4.22 | q, 4.2 |
| 5' | 61.0 | 3.62, 3.73 | m |
| 23, 16 | 60.3-60.8 | 4.25-4.39 | m |
| 17, 24 | 14.1-14.2 | 1.28-1.38 | m |
| 18 (major) | — | 12.51 | d, 12.4 |
| 18 (minor) | — | 11.47 | d, 13.0 |
| 2'-OH (major) | — | 5.63 | d, 6.1 |
| 2'-OH (minor) | — | 5.62 | d, 6.1 |
| 3'-OH | — | 5.30 | d, 5.1 |
| 5'-OH | — | 5.08 | t, 5.5 |

The compound of formula (4) was confirmed to be a mixture of the following two isomers:

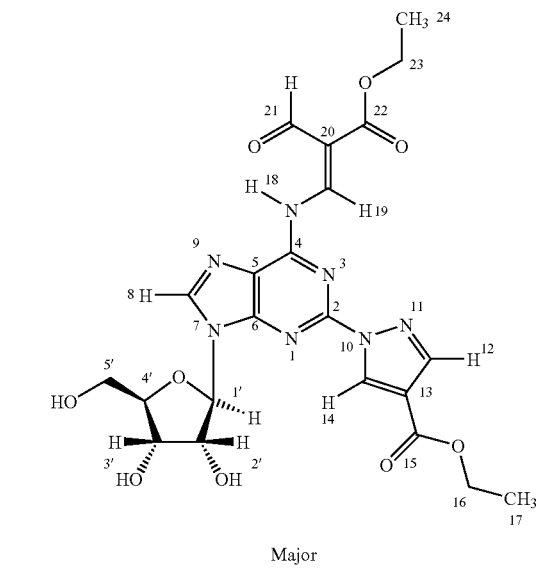

Major

-continued

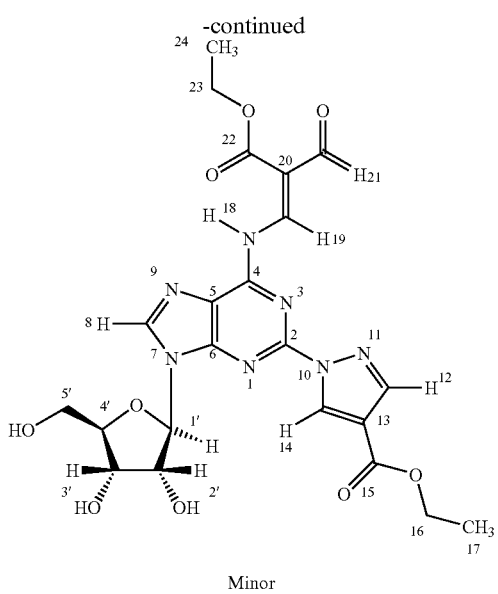

Minor

EXAMPLE 6

Preparation of (1-{9-[(4S,2R,3R,5R)-3,4-dihydroxy-5-(hydroxymethyl)oxolan-2-yl]-6-aminopurin-2-yl}pyrazol-4-yl)-N-methylcarboxamide from Compound (4)

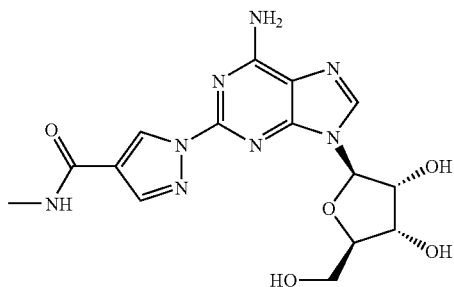

Aqueous 40% methylamine solution (1300 ml) was placed in a pressure reactor, cooled to 0-5° C., and the product of Example 5 (ethyl (2E)-3-({9-[(4S,2R,3R,5R)-3,4-dihydroxy-5-(hydroxymethyl)oxolan-2-yl]-2-[4-(ethoxycarbonyl)pyrazolyl]purin-6-yl}amino)-2-formylprop-2-enoate (100 g) added. The mixture was stirred at 0-5° C. for at least 8 hours, monitoring the reaction for completion. When complete, the mixture was warmed, maintaining the temperature between 50 and 60° C. for 1 hour, and then cooled to less than 30° C. over a period of 1 hour. When the temperature was below 30° C., the mixture was degassed using a pressure of 100-150 mm Hg, allowing the temperature to decrease to 0-5° C. The mixture was stirred at 0-5° C. for at least 1 hour, maintaining the pressure at 100-150 mm Hg. The vacuum was then discontinued and replaced by nitrogen, maintaining the temperature at 0-5° C. for not less than 30 minutes. The solid product was then filtered off, washed with water (3×500 ml), then with absolute ethanol (625 ml). The product was dried under vacuum, not allowing the temperature to exceed 40° C., to provide (1-{9-[(4S,2R,3R,5R)-3,4-dihydroxy-5-(hydroxymethyl)oxolan-2-yl]-6-aminopurin-2-yl}pyrazol-4-yl)-N-methylcarboxamide as its monohydrate.

$^1$H and $^{13}$C NMR spectra were obtained in the following manner. Two samples of the material obtained above were weighed out and dissolved in $d_6$-DMSO-5.3 mg was used for the $^1$H spectra, and 20.8 mg was used for $^{13}$C spectra. All spectra were acquired at ambient temperature on a JEOL Eclipse$^+$ 400 spectrometer operating at 400 MHz for $^1$H and 100 MHz for $^{13}$C.

| Label | $^{13}$C shift (ppm) | $^1$H shift (ppm) | Multiplicity, splitting (Hz) |
| --- | --- | --- | --- |
| 2 | 150.5 or 150.3 | — | |
| 4 | 156.4 | — | |
| 4a | 117.9 | — | |
| 6 | 140.0 | 8.41 | s |
| 7a | 150.5 or 150.3 | — | |
| 1' | 86.9 | 5.94 | D, 6.2 |
| 2' | 73.7 | 4.62 | m |
| 2'-OH | — | 5.50 | D, 6.2 |
| 3' | 70.5 | 4.17 | m |
| 3'-OH | — | 5.23 | D, 4.7 |
| 4' | 85.7 | 3.96 | m |
| 5' | 61.5 | 3.67, 3.57 | m |
| 5'-OH | — | 5.02 | D, 5.7 |
| A | 140.9 | 8.07 | D, 0.8 |
| B | 120.2 | — | |
| C | 129.6 | 8.95 | D, 0.8 |
| D | 161.7 | — | |
| E | 25.6 | 2.76 | D, 4.6 |
| NH$_2$ | — | 7.77 | br s |
| NH | — | 8.35 | Q, 4.6 |

An elemental analysis gave the following results: C, 43.96%; H, 4.94%; N, 27.94. Theoretical: C, 44.12%; H, 4.94%; N, 27.44%; O, 27.09. The analysis corresponds within experimental error limits to the monohydrate.

We claim:

1. A method for the large scale preparation of (1-{9-[(4S,2R,3R,5R)-3,4-dihydroxy-5-(hydroxymethyl)oxolan-2-yl]-6-aminopurin-2-yl}pyrazol-4-yl)-N-methylcarboxamide:

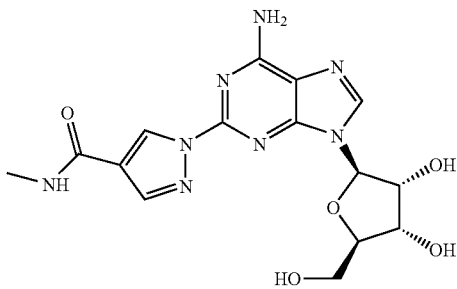

comprising:

reacting a compound of the formula (3)

(3)

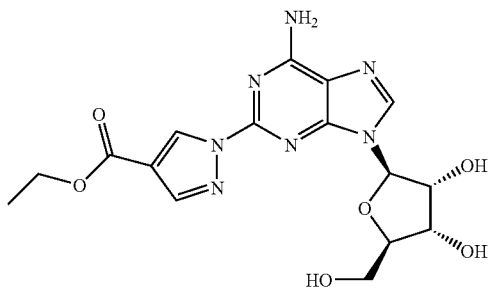

with methylamine wherein the compound of formula (3) is reacted with an aqueous solution of methylamine at an initial temperature of about 0-5° C. followed by warming to about 50-70° C. in a sealed pressure reactor.

2. The method of claim 1, further comprising wherein the (1-{9-[(4S,2R,3R,5R)-3,4-dihydroxy-5-(hydroxymethyl)oxolan-2-yl]-6-aminopurin-2-yl)pyrazol-4-yl)-N-methyl-carboxamide end product is isolated as the pure monohydrate by (a) dissolving the product in a solvent,
(b) adding purified water,
(c) filtering the slurry thus formed,
(d) washing the contents of the filter with water followed by ethanol, and
(e) drying the solid that remains under vacuum at a temperature that does not exceed 40° C.

3. The method of claim 2, wherein the solvent of step (a) is dimethylsulfoxide.

4. A method of preparing a compound of the formula (3):

(3)

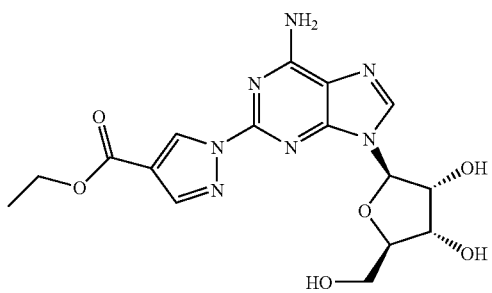

comprising:

reacting a compound of the formula (2)

(2)

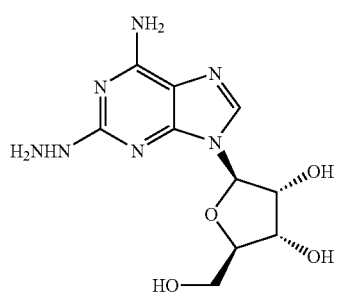

with ethyl 2-formyl-3-oxopropionate wherein about 1.1 molar equivalent of ethyl 2-formyl-3-oxopropionate is reacted with the compound of formula (2) in a solvent.

5. The method of claim 4, wherein the solvent is ethanol.

6. The method of claim 5, wherein the reaction is conducted at a temperature of about 80° C.

7. A method of synthesizing (1-{9-[(4S,2R,3R,5R)-3,4-dihydroxy-5-(hydroxymethyl)oxolan-2-yl]-6-aminopurin-2-yl}pyrazol-4-yl)-N-methylcarboxamide

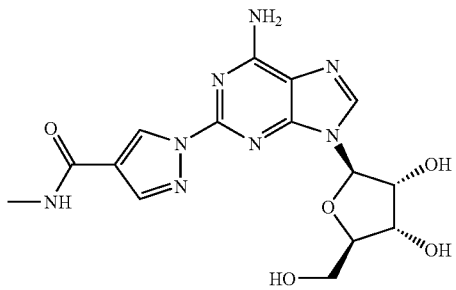

comprising by contacting a compound of the formula (4):

(4)

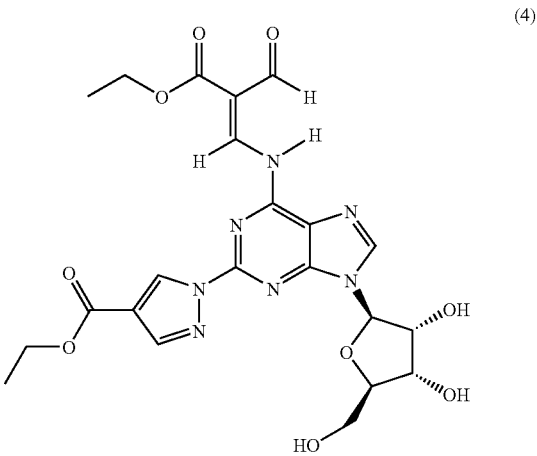

with an aqueous solution of methylamine at an initial temperature of about 0-5° C. followed by warming to about 50-70° C. in a sealed pressure reactor.

8. The method of claim 7, further comprising wherein the (1-{9-[(4S,2R,3R,5R)-3,4-dihydroxy-5-(hydroxymethyl)oxolan-2-yl]-6-aminopurin-2-yl}pyrazol-4-yl)-N-methyl-carboxamide end product is isolated as the pure monohydrate by (a) dissolving the product of claim 7 in a solvent,
(b) adding purified water,
(c) filtering the slurry thus formed,
(d) washing the contents of the filter with water followed by ethanol, and
(e) drying the solid that remains under vacuum at a temperature that does not exceed 40° C.

9. The method of claim 8, wherein the solvent of step (a) is dimethylsulfoxide.

10. A method of synthesizing a compound of the formula (4):

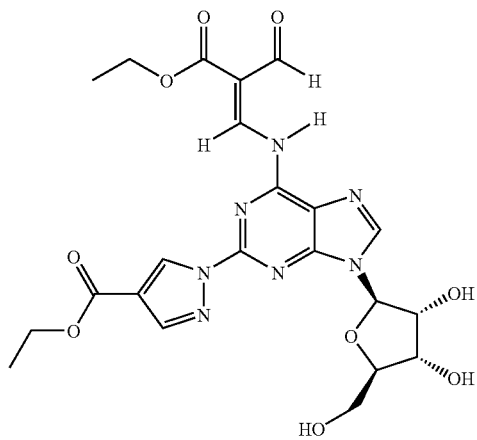

comprising
contacting a compound of the formula (2):

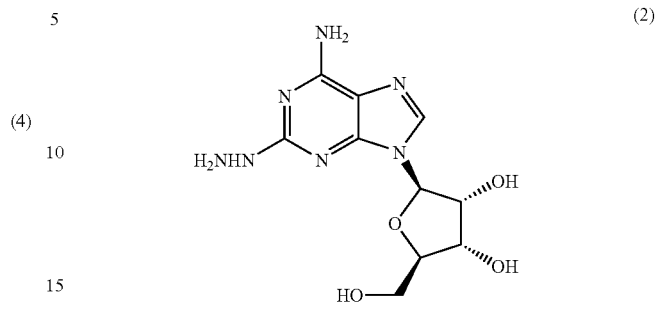

with an excess of ethyl 2-formyl-3-oxopropionate wherein about a 2-10 fold molar excess of ethyl 2-formyl-3-oxopropionate is reacted with the compound of the formula (2) in a solvent.

11. The method of claim 10, wherein the solvent is ethanol.

12. The method of claim 11 wherein the reaction is conducted at a temperature of about 80° C.

13. The method of claim 10, wherein about a 5-10 fold molar excess of ethyl 2-formyl-3-oxopropionate is reacted with the compound of the formula (2).

* * * * *

UNITED STATES PATENT AND TRADEMARK OFFICE
CERTIFICATE OF CORRECTION

| | | |
|---|---|---|
| PATENT NO. | : 7,732,595 B2 | Page 1 of 1 |
| APPLICATION NO. | : 11/701699 | |
| DATED | : June 8, 2010 | |
| INVENTOR(S) | : Zablocki et al. | |

It is certified that error appears in the above-identified patent and that said Letters Patent is hereby corrected as shown below:

Title Page, Item (75) Inventors, should read

-- (75)    Inventors:    Jeff Zablocki, Mountain View, CA (US);
                              Elfatih Elzein, Fremont, CA (US);
                              Robert Seemayer, Belmont, CA (US);
                              Travis Lemons, Los Altos Hills, CA (US) --.

Signed and Sealed this
Eighth Day of March, 2016

Michelle K. Lee
*Director of the United States Patent and Trademark Office*